United States Patent [19]

Kende et al.

[11] 4,154,745

[45] May 15, 1979

[54] ISOBENZOFURAN ROUTE TO ANTHRACYCLOQUINONES

[75] Inventors: Andrew S. Kende, Pittsford, N.Y.; Yuh-Geng Tsay, Taichung, Taiwan

[73] Assignee: Research Corporation, New York, N.Y.

[21] Appl. No.: 894,090

[22] Filed: Apr. 6, 1978

Related U.S. Application Data

[62] Division of Ser. No. 792,684, May 2, 1977, Pat. No. 4,116,981.

[51] Int. Cl.² .................. C07C 49/62; C07C 49/70; C09B 3/62; C07D 307/69
[52] U.S. Cl. .................................. 260/376; 260/365; 560/139; 260/351; 260/396 R; 260/346.71
[58] Field of Search ............... 560/139; 260/351, 365, 260/396 R, 346.71, 376

[56] References Cited

U.S. PATENT DOCUMENTS

| | | | |
|---|---|---|---|
| 3,109,007 | 10/1963 | Blackwood et al. | 260/346.71 |
| 3,518,282 | 1/1970 | Schaller et al. | 260/346.71 |
| 3,665,018 | 5/1972 | Jolles | 260/365 |
| 4,012,448 | 3/1977 | Smith et al. | 260/365 |
| 4,020,270 | 4/1977 | Arcamone et al. | 260/365 |

FOREIGN PATENT DOCUMENTS

| | | | |
|---|---|---|---|
| 538362 | 3/1957 | Canada | 260/396 |
| 1164582 | 10/1958 | France | 260/396 |

*Primary Examiner*—Patrick Garvin
*Assistant Examiner*—Raymond Covington
*Attorney, Agent, or Firm*—Omri M. Behr

[57] ABSTRACT

There is provided a novel method of synthesizing certain tetracyclic quinones. In particular, there is provided a novel route to the synthesis of (±)-7-deoxydaunomycinone and analogs thereof which includes the provision of novel tetrahydronaphthoquinones and tetracyclic quinone intermediates. The compounds of the present invention are provided through a route comprising a Diels-Alder addition of certain isobenzofurans to certain novel tetrahydronaphthoquinones. The products of the synthetic route provided herein may be converted into compounds of known antibiotic and antineoplastic activity.

6 Claims, No Drawings

ISOBENZOFURAN ROUTE TO ANTHRACYCLOQUINONES

This is a division of application Ser. No. 792,684, filed May 2, 1977, now U.S. Pat. No. 4,116,981.

BACKGROUND OF THE INVENTION

Certain antibiotics having antineoplastic activity—for example, adriamycin and related compounds—are known in the art. Adriamycin is described as being obtained by a microbiological process in U.S. Pat. No. 3,590,028 to Arcamone et al. Certain semi-synthetic procedures for making these compounds are described in U.S. Pat. No. 3,803,124 also to Arcamone et al. Certain synthetic intermediates—in particular, those directed to the preparation of daunomycin and 4-demethoxydaunomycin—are disclosed in U.S. Pat. No. 3,963,760 to Bernardi and Patelli. Other related compounds are dicslosed by Patelli et al in Belgian Pat. No. 830,090 assigned to Societa Farmaceutici Italia S.p.A. A total synthetic route to daunomycin is disclosed in Application Ser. No. 632,939 of the present Applicants with another co-worker and a related synthetic sequence directed to the 4-demethoxydaunomycin and, inter alia, dimethyl-4-demethoxydaunomycin are disclosed in U.S. Pat. No. 4,021,457 of May 3, 1977 to the same Applicants.

SUMMARY OF THE INVENTION

There is provided a novel process for the preparation of certain polycyclic quinones—in particular, tetracyclic quinones—whereby there is provided a route to the synthesis of 7-deoxydaunomycinone, 7-deoxy-4-demethoxydaunomycinone, and 7-deoxy-4-demethoxymethyl, and -dimethyldaunomycinone. The synthetic sequence comprises the Diels-Alder addition of the appropriate isobenzofuran to a novel tetrahydronaphthoquinone to provide a tetracyclic quinone which is converted, in four steps, to the desired known intermediate.

There are further disclosed procedures for preparing the aforesaid novel tetrahydronaphthoquinone as well as procedures for preparing certain isobenzofurans which were not heretofore available.

It should be noted that, while the numbering of the compounds in the flow sheets set forth below is internally sequential, it has been found convenient to utilize a separate decade of numbering for each sequence. Hence, certain numbers in certain decades are not utilized.

SEQUENCE A

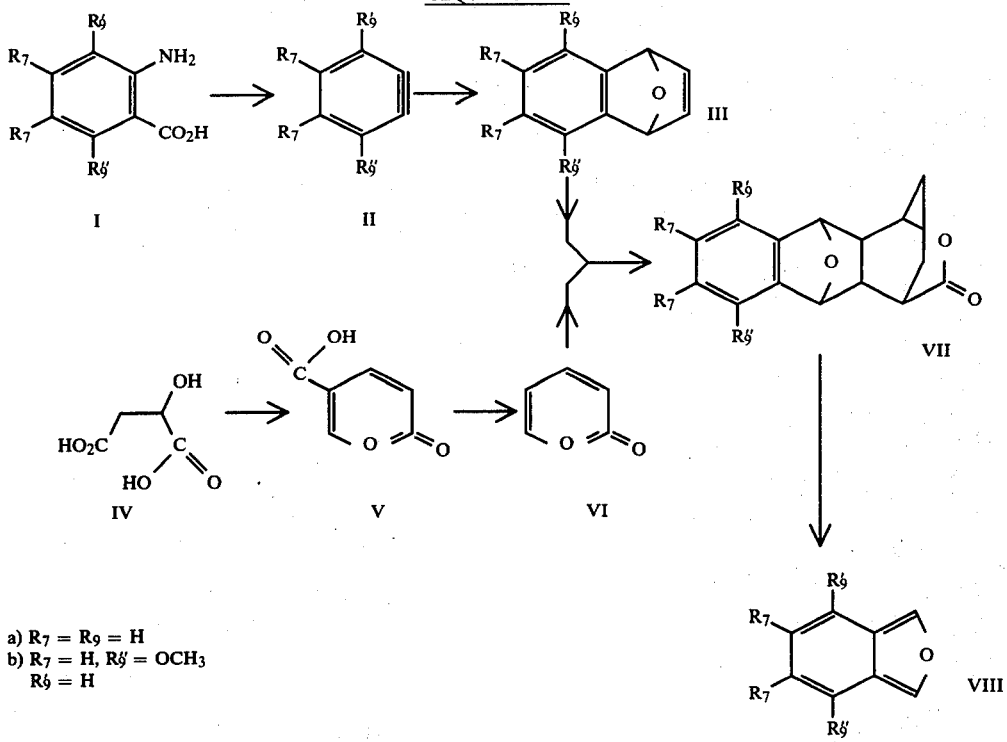

a) $R_7 = R_9 = H$
b) $R_7 = H$, $R_9' = OCH_3$
$R_9 = H$

The isobenzofurans of the present invention are provided by the reaction sequence shown as Sequence A above. In this reaction sequence, $R_7$ is hydrogen or lower alkyl and $R_9$ is hydrogen, lower alkyl or lower alkoxy, phenyl- or substituted phenyl-lower alkyl, wherein the prefix "lower alk" signifies a hydrocarbon moiety of 1 to 5 carbon atoms, or halo. In the reaction scheme, $R_9'$ and $R_9''$ are differentiated by the "prime indicator" since the prime designated constituent may have any of the values shown in the group and may be the same as, or different from, the other member of the group.

In the reaction Sequence A above, the appropriate aminobenzoic acid I is diazotized to form the unisolated benzyne intermediate II which is trapped with furan to provide the tricyclic Diels-Alder adduct III. Coumalic acid V is heated with copper to provide the pyrone VI which is reacted with the tricyclic adduct III to form the pentacyclic Diels-Alder adduct VII. The pentacyclic adduct VII may then be thermally dissociated to form the desired isobenzofuran VIII. Since the isobenzofuran has a tendency to deteriorate rapidly—that is to say, by oxidation or polymerization—the isobenzofuran VIII is not usually isolated, but its precursor VII is utilized in the principal reaction sequence wherein it is thermally decomposed in situ.

While the foregoing reaction sequence is known in the literature for the preparation of isobenzofuran itself (i.e., Compound VIIIa), where $R_9'$ as distinguished from $R_9''$ is lower alkoxy, Compound III is not formed and, thus, the readily available 2-amino-3-methoxybenzoic acid, for example, cannot be utilized to make the appropriate monomethoxy tricyclic adduct III. Since it does not make any difference, in the ultimate reaction sequence where a single alkoxy moiety is present in (i.e., the 4- or 7- positions) the benzofuran ring, there is utilized as the appropriate benzyne precursor, the regioisomer thereof—namely, the 2-amino-6-alkoxybenzoic acid I.

The precursor for the AB ring system of the anthracycloquinones is prepared in accordance with Scheme B below. It should be noted that Compounds X through and including the tetralone XIII are known compounds.

The tetralone XIII is then ethynylated, suitably with ethynyl magnesium Grignard, and, the thus produced ethynylcarbinol XIV is hydrated with a mercuric alkanoate, suitably mecuric acetate, to provide the tetralin XV which, in turn, is oxidized to the bicyclic quinone XVI. This oxidation is suitably carried out with argentic oxide in acetone. Other agents, such as aluminum chloride followed by lead tetraacetate, are operative but not preferred.

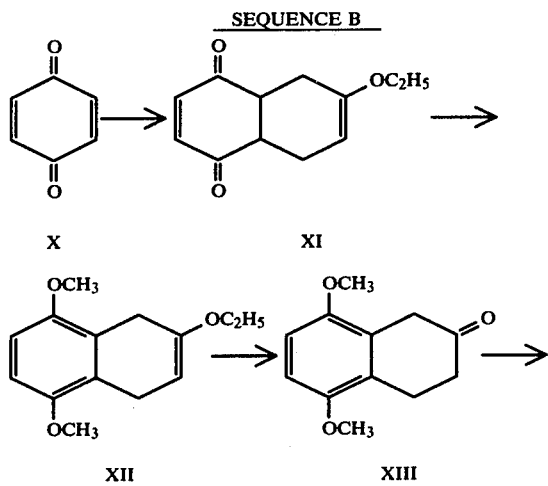

SEQUENCE B

X    XI

XII    XIII

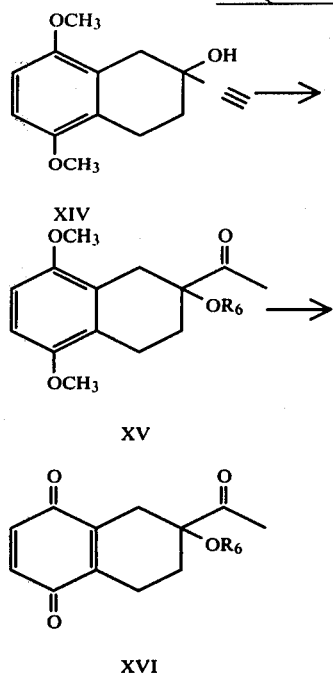

-continued
SEQUENCE B

XIV

XV

XVI

The isobenzofuran VIII (or its immediate precursor VII) is then reacted with the bicyclic quinone XVI to provide the Diels-Alder adduct XX. Diels-Alder adduct XX is subjected to selective aromatization followed by reductive acylation suitably in the presence of the desired acyl anhydride, suitably an alkanoic anhydride, such as acetic anhydride, to provide the triacylate XXII. Oxidation of the aromatic C ring provides the quinone XXIII. Where this oxidation is allowed to proceed for too long a time, a further ketone function would be provided at the C-7 position on the A ring.

In the normal reaction sequence, the triacylated quinone XXII is hydrolyzed to provide the known trihydroxy ketone XXIV which, in turn, is hydroxylated at C-7 by methods known to the art to provide the known (±)-4-demethoxydaunomycinone and its corresponding D ring substituted analog (XXV). This end product may also be obtained by protection of the side chain ketone suitably by ketalization (to XXVI) followed by over oxidation to the 7-ketone ketal XXVII and reduction, preferably with sodium borohydride, followed by epimerization and acid hydrolysis to the desired XXV.

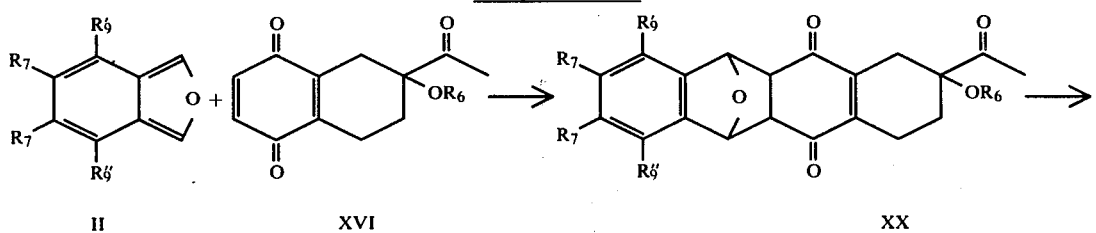

SEQUENCE C

II    XVI    XX

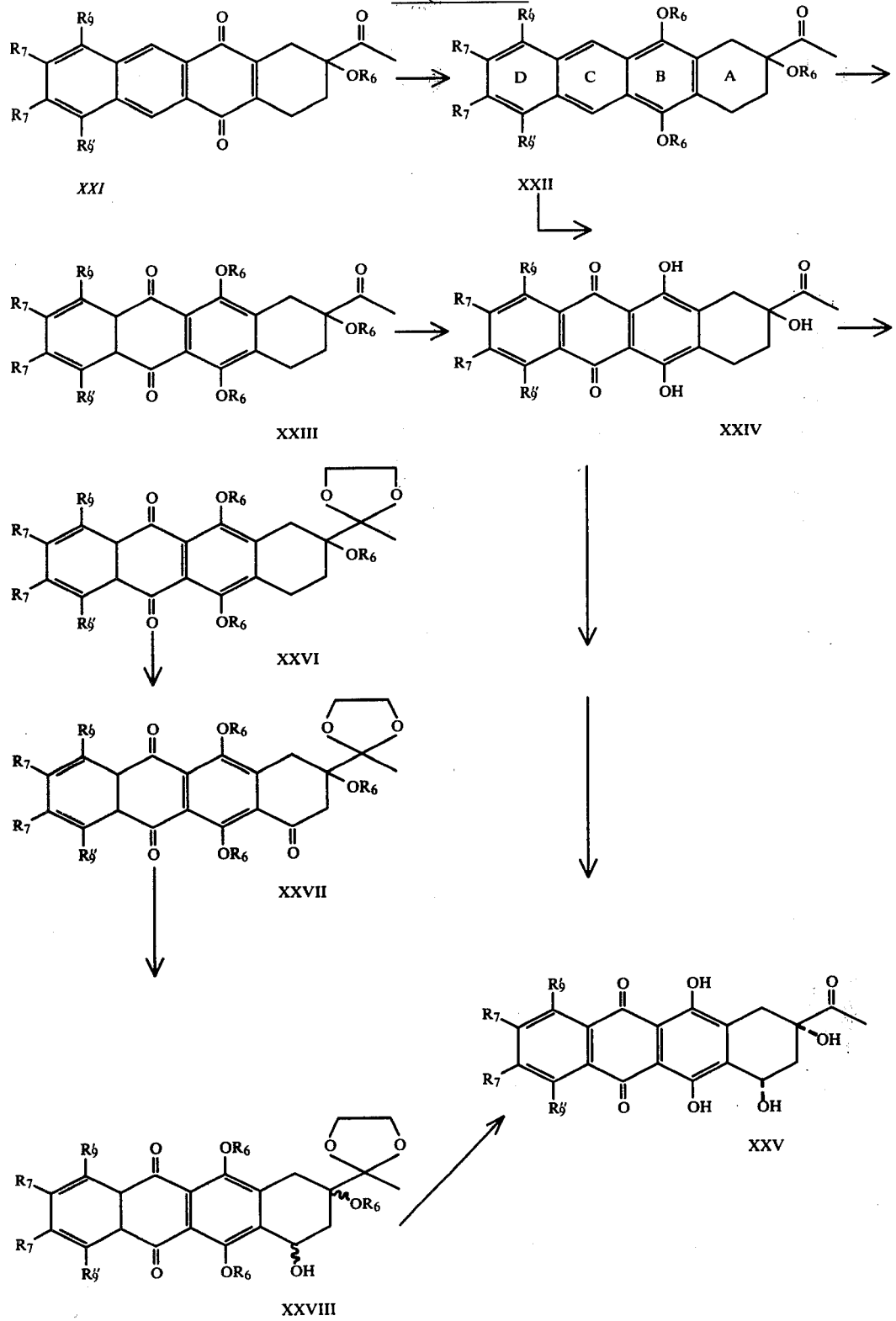

DESCRIPTION OF THE PREFERRED EMBODIMENTS

The reaction sequence for the preparation of isobenzofuran itself—that is to say, Compound VIIIa or its immediate precursor which is actually utilized in the process of the present invention—is carried out in accordance with the method of Fieser and Haddadin (Can. J. Chem. 43 1599 (1965)). This method may be employed as well where $R_7$ is lower alkyl and where $R_9'$ and $R_9''$ are other than alkoxy. The method is not, however, operative where $R_9'=R_9''=$alkoxy since, it is believed, that the alkoxy group vicinal to the amino group prevents the formation of the benzyne II due to resonance stabilization.

The method is, however, operative where $R_9'$=hydrogen and $R_9''$=alkoxy—that is to say, the alkoxy group is vicinal to the carboxy moiety—and this embodiment is used where a mono substitution in the D ring of the tetracyclic quinonoid end products is desired since the same regioisomers would be produced regardless of whether a single alkoxy group is present in the 4- or 7-positions of the isobenzofuran moiety VIII.

In the preferred embodiments of the invention, certain combinations of the $R_7$ and $R_9$ moieties are preferred, especially preferred are those where all $R_7$ and $R_9$ groups are hydrogen. Where the $R_7$ groups are other than hydrogen, the $R_9$ groups are hydrogen and, conversely, where the $R_9$ groups are other than hydrogen, the $R_7$ groups are hydrogen. The preferred products of this invention, thus, are mono or bisubstituted in the 1- and 4- or 2- and 3-positions of the tetracyclic moieties provided, however, that ether groups are present either at the 1- or at the 4-positions.

The $R_7$ moieties may be hydrogen, alkyl, suitably lower alkyl of 1–5 carbon atoms, in a branch or straight chain—for example, methyl, ethyl, propyl, isopropyl, butyl, isobutyl, tertbutyl, pentyl, isopentyl, or the like. They may be phenyl- or substituted phenyl lower alkyl where the substituents are lower alkyl, lower alkoxy, or halo where the "lower alk" moiety contains 1–5 carbon atoms in a straight or branch chain. They may also be halogen, suitably chlorine or bromine.

The $R_9$ moieties have the values of hydrogen, lower alkyl, phenyl lower alkyl and substituted pheny lower alkyl, as well as lower alkoxy, when these moieties are as defined for $R_7$, as well as halogen as defined in $R_7$.

$R_6$ is lower alkanoyl of 1–5 carbon atoms such as formyl, acetyl, propionyl, butyryl, or valeryl or the like, or phenyl lower alkanoyl such as benzoyl, phenylacetyl, phenylpropionyl, phenylbutyryl, and the like.

Thus, the appropriate 2-amino-6-alkoxybenzoic acid I is diazotized and condensed with furan in accordance with the procedures of reaction sequence A and, similarly, subsequently added to alpha pyrone to give the corresponding isobenzofuran precursor. In the case of the precursor for the 4-methoxyisobenzofuran, this is VIIb.

As stated hereinabove, Compound XIII is a known compound (Lewis et al J. Am. Chem. Soc. 74 5321 (1952)). This tetralone is then ethynylated to provide the carbinol XIV. Such ethynylation may be carried out utilizing an alkali metal ethyne such as lithium ethyne or utilizing an ethynyl magnesium halide. It has been found that the use of the latter—that is to say, the Grignard reagent—gives substantially superior results. There is prepared, in the usual manner, a substantial excess, suitably about 3 moles per mole of tetralone XIII to be used, of ethynyl magnesium halide, suitably bromide, an ethereal solvent, suitably tetrahydrofuran, dioxan or diethyl ether.

In this procedure, ethyl magnesium bromide is added to a saturated solution of acetylene in tetrahydrofuran in an inert atmosphere. The passage of acetylene gas is continued and the tetralone XIII in, suitably, tetrahydrofuran is added. After completion of the tetralone addition, the passage of acetylene is continued for a short time, suitably for about one hour, and thereafter, the reaction mixture held at ambient temperature overnight.

The reaction mixture is then quenched, preferably by the addition of cold saturated ammonium chloride solution, or aqueous oxalic acid, the organic (ethereal) phase set aside and retained, and the aqueous phase extracted with a suitably non-hydroxylic, water immiscible, organic solvent, preferably ethyl acetate. The ethyl acetate extract and the ether extract are then combined, dried, and evaporated to dryness to yield the ethynyl carbinol XIV. This residue may be further purified.

The manner of purification is not critical and will depend upon the quantities available. It has been found that chromatography on silica, utilizing as an eluent a mixture of an alkanol with an alkylene halide, suitably 3% methanol in methylene chloride may be employed.

The thus produced ethynyl carbinol (XIV) is then hydrated to form the corresponding tetralin XV. In this procedure, the ethynyl carbinol XIV is taken up in a reaction inert polar organic solvent, suitably a halogenated hydrocarbon such as chloroform, methylene chloride or the like, or in an alkyl alkanoic such as ethyl acetate, the latter being especially preferred. There is also prepared a fresh solution of mercuric ion. The source of mercuric ion is not critical—salts of mineral acid such as mercuric sulfate or salts of organic acids such as mercuric acetate or yellow mercuric oxide itself may be employed. It is especially preferred, however, to utilize mercuric acetate.

In this procedure, a substantial excess, suitably between about 2 to about 3 moles of mercuric acetate per mole of carbinol XIV are stirred in the above polar solvent at ambient temperature in an inert atmosphere, suitably a nitrogen atmosphere, for about eight to about eighteen hours. The reaction is then quenched by the addition of gaseous hydrogen sulfide until no further black precipitate is formed. The black precipitate (of mercuric sulfide) is removed by filtration reaction mixture and the filtrate worked up in the usual manner to provide the desired tetralin XV. The The tetralin XV is then oxidized to the corresponding benzoquinone XVI. The tetralin XV is taken up in a reaction inert, water miscible organic solvent. In view of the fact that the present step involves oxidation, said solvent should be relatively inert to oxidation. It has been found that ketones, suitably dialkyl ketone, preferably acetone, may be utilized. It is further preferred that the solvent be heated to a temperature at or near its boiling point. To the warm solution is added a substantial excess of the oxidizing agent. It is preferred to utilize 2 to 6 moles, suitably about 3 to about 5 moles, of oxidizing agent per mole of tetralin XV. It has been found advisable to briefly sonicate the mixture to obtain uniform dispersal of the oxidant. Among the oxidizing agents which may be used silver (II) oxide (argentic oxide) is especially preferred. The reaction is then initiated by the addition of a small amount of acid, suitably mineral acid, preferably 6 N nitric acid. The reaction is rapid and should be considered complete within three to ten minutes.

The acid utilized should be a strong acid; however, the quantity thereof is more critical than its nature. The amount of acid utilized should be just sufficient to dissolve all of the silver oxide. If an amount substantially greater than this is employed, the water present in the acid will interfere with the reaction and lower the yields obtained. The reaction is quenched by the addition of water and the reaction mixture is then extracted, suitably with a water immiscible reaction organic solvent, suitably an halogenated hydrocarbon solvent such as chloroform.

The isobenzofuran VIII, or its immediate precursor VII, is then condensed with the benzoquinone XVI in a Diels-Alder reaction.

As stated heretofore, the isobenzofurans are generally not stable and tend to deteriorate rapidly. On the other hand, they are very readily generated in situ from the corresponding pentacyclic lactone VII by thermolysis. In the preferred procedure, the lactone VII is taken up in a reaction inert water and hydrocarbon miscible solvent, especially suitably are the ethers of ethylene glycol, most preferably the dialkyl ethers of diethylene glycol such as, for example, diglyme. In this procedure, the bicyclic quinone XVI is taken up in the solvent and heated under an inert atmosphere, suitably a nitrogen atmosphere, for from five to ten minutes at a temperature slightly below reflux—that is to say, between 130° and 150° C. Thereafter the appropriate lactone VII is added portion-wise in slight excess, suitably a 10% excess. The reaction mixture is very briefly heated for a few minutes, cooled to ambient temperature, and quenched with water which causes the Diels-Alder adduct to precipitate. The adduct XX is removed by filtration and dried under reduced pressure.

The C ring, containing the oxa-bridge, is then aromatized to the corresponding anthraquinone XXI. In this procedure, the Diels-Alder adduct XX is taken up in an anhydrous alkanoic acid, suitably a lower alkanoic acid—for example, glacial acetic acid—and heated, suitably under reflux and in an inert atmosphere, suitably a nitrogen atmosphere, in the presence of the appropriate alkali metal alkanoate—for example, where acetic acid is used as a solvent, anhydrous sodium acetate. It is especially preferred to employ substantially exactly two moles of the alkanoate per mole of Diels-Alder adduct. The reaction mixture is heated from between about eight to about eighteen hours approximately, cooled to ambient temperature, and quenched with water which causes the appropriate anthraquinone XXI to be precipitated. The precipitate is removed by filtration and dried under reduced pressure. The compound may, if desired, be further purified by chromatography on silica gel.

Such purification, however, is not necessary for the next step in the synthetic sequence.

The anthraquinone XXI is then subjected to reductive acylation. The reductive acylation is carried out with a suitable reducing agent in the presence of an appropriate acyl anhydride. It is preferred to utilize an alkanoyl anhydride, suitably a lower alkanoyl anhydride such as acetic anhydride, and the preferred reducing agent is zinc dust.

The reaction mixture is heated, suitably under reflux, for approximately five to fifteen minutes in an inert suitably a nitrogen, atmosphere. The reaction mixture is cooled, the excess zinc removed by filtration, the filtrate quenched with warm water, and the aqueous mixture extracted with a polar water immiscible solvent, suitably a halogenated hydrocarbon such as chloroform. The extract is worked up in the usual manner to yield the naphthacene XXII as a residue which may, if desired, be further purified by chromatography.

The aromatic C ring of the naphthacene XXII is oxidized to the corresponding quinone. This oxidation proceeds rather readily. In the preferred procedure, the naphthacene XXII is taken up in acetic acid, suitably 80% acetic acid, and treated with an excess of chromium trioxide in a similar solvent. Where it is desired that the reaction not proceed beyond the naphthacenedione XXIII, there should be utilized no more than 4 equivalents of chromium trioxide per mole of the naphthacene XXII and that the reaction should not be allowed to proceed under conditions more vigorous than ambient temperature for more than three hours.

In the event that more vigorous conditions are employed or a greater excess of chromium trioxide is utilized, there will be provided the corresponding naphthacenetrione having a keto group at the 7 position of the A ring. If this product is desired, however, as set out in sequence C XXVI through XXV, the naphthacene XXII is protected. This protection is suitably carried out by ketalization using an alkylene glycol, suitably a lower alkylene glycol such as ethylene glycol and a catalytic amount of acid. There may be utilized, as for example, p-toluenesulfonic acid or zinc chloride in anhydrous conditions, without a co-solvent or with a co-solvent, such as benzene. The reaction mixture is heated at between 50° C. and 100° C. for from one to ten hours. Under conditions of ketalization some loss of the $R_6$ acyl moiety is to be anticipated. In the event that this occurs, as shown by, say, a spectroscopic check of the reaction product, this unpurified ketal is reacylated in the usual manner, suitably by reaction with acetic anhydride in the presence of sodium acetate, zinc chloride, or pyridine.

Hydrolysis of the naphthacenedione XXIII to remove the alkanoyl moieties is then carried out, suitably under acid conditions. It is preferred to take up the naphthacenedione triester XXIII in a water miscible, polar organic solvent, suitably acetic acid or ethanol, which mixture is then acidified, preferably with an excess of concentrated mineral acid, preferably 6 N hydrochloric acid, and the mixture heated for from about one to about three hours at from about 50 to about 80, suitably from about 65° to about 70° C. The reaction product is then quenched with water and extracted with a water immiscible polar solvent, suitably an halogenated hydrocarbon solvent such as chloroform, which is then worked up in the usual manner to give the known trihydroxy naphthacenedione XXIV.

This trihydroxy compound may then be converted to the corresponding 7-hydroxy compound by methods disclosed, say, in U.S. Pat. No. 4,021,457.

Where it is desired to proceed with the ketal XXVI, treatment with a substantial excess—i.e., 4 to 8 equivalents of chromium trioxide per mole of naphthacene—yields the 7-ketoketal XXVII which is then reduced with sodium borohydride to yield the 7-hydroxy ketal XVIII. It should be noted that such reduction will yield the compound having the 7-hydroxy group in a cis orientational relationship with the 9-acyloxy group as well as in trans orientation therewith.

This stereo isomeric mixture is converted to the desired cis orientation by reaction with trifluoroacetic acid for about two hours in accordance with the procedures of U.S. Pat. No. 4,021,457. The reaction product is not isolated, but subjected to acid hydrolysis to yield the desired tetrahydroxynaphthacenedione XXV. In the following Examples, the units of nmr data are δ; of infra-red are μ; and ultraviolet are nm.

EXAMPLE I

1,4-Dihydronaphthalene-1,4-endo-oxide (IIIa)

Solutions of 20 ml of isoamyl nitrite in glyme (20 ml) and of 13.7 g of anthranilic acid in glyme (45 ml) were added simultaneously by drops to a refluxing mixture of glyme (50 ml) and furan (50 ml). Refluxing was continued for ten minutes and the brown solution was cooled, made basic with aqueous sodium hydroxide (1 N), and extracted with petroleum ether. The extract was washed thoroughly with water, clarified with Norit ®, dried, and evaporated to give an oil. The oil solidified on cooling to give 7 g (51% yield) of light yellow solid. Recrystalization of the yellow solid from petroleum ether gave colorless crystalline solid of 1,4-dihydronaphthalene-1,4-endo-oxide (IIIa), m.p. 53°–54° C. (lit. m. p. 56° C.).

nmr: (CDCl$_3$; 60 MHz) 7.25–6.75 (m, 6H), 5.62 (s, 2H), ir: (KBr) 7.02; 7.53; 7.93 ms: m/e+ 144 (M+; 28.0%), 128 (33.0%), 118 (30.0%) 116 (81.0%), 115 (100%), 89 (18.0%).

EXAMPLE II

1,4-Carbonyloxy-9,10-oxido-1,4,9,9a,10,10a-hexahydroanthracene (VIIa)

1,4-Dihydronaphthalene-1,4-endo-oxide (IIIa) was dissolved in α-pyrone (2 g) and the solution left to stand at room temperature under nitrogen for four days, during which time the adduct crystallized. The crystalline mass was broken up, filtered and washed with cold methanol to give 4.2 g (87.5% yield) of 1,4-carbonyloxy-9,10-oxido-1,4,9,9a,10,10a-hexhydroanthracene (VIIa), m.p. 105°–107° C. (lit. m.p. 105°–107° C.)

nmr: (CDCl$_3$; 100 MHz) 7.16 (s, broad, 4H), 6.48 (t, 2H), 5.28 (m, 1H), 5.04 (d, 2H), 3.70 (m, 1H), 2.70 (q, 1H), 2.25 (q, 1H).

ir: (KBr) 5.72

EXAMPLE III

5-Methoxy-1,4-dihydronaphthalene-1,4-endo-oxide (IIIb)

Solutions of 3.2 ml of isoamyl nitrile in glyme (6.8 ml) and of 3.2 g of 2-amino-6-methoxybenzoic acid (Ib) in glyme (6 ml) were added simultaneously by drops to a refluxing mixture of glyme (10 ml) and furan (15 ml). Refluxing was continued for twenty minutes and the reaction mixture cooled. The solution was made basic with aqueous sodium hydroxide (1 N), and extracted with hexane. The extract was washed thoroughly with water, dried, and evaporated to give an off-white solid. Recrystallization of the solid from hexane gave 1.59 g (45% yield) of 5-methoxy-1,4-dihydronaphthalene-1,4-endo-oxide (IIIb), m.p. 58°–60° C.

nmr: (CDCl$_3$; 100 MHz) 7.01–6.48 (m, 4H), 5.92 (s, 1H), 5.65 (s, 1H), 3.80 (s, 3H).

ir: (KBr) 6.20; 6.78 ms: m/e+ 174 (M+; 27.0%), 159 (14.1%), 148 (34.1%), 146 (100%), 131 (52.9%), 115 (82.4%), 103 (51.8%).

Analysis: Calculated for C$_{11}$H$_{10}$O$_2$: C, 75.86; H, 5.75. Found: C, 75.40; H, 5.74.

In accordance with the above procedure but where, in place of 2-amino-6-methoxybenzoic acid, there is used 2-amino-6-butoxybenzoic acid, 2-amino-6-methylbenzoic acid, 2-amino-6-chlorobenzoic acid, 2-amino-6-bromobenzoic acid, 2-amino-6-benzylbenzoic acid, 2-amino-6-chlorobenzylbenzoic acid, 2-amino-3,6-diethylbenzoic acid, 2-amino-3,6-dichlorobenzoic acid, 2-amino-3,6-dibenzylbenzoic acid, 2-amino-4-butylbenzoic acid, 2-amino-4-methylbenzoic acid, 2-amino-4-chlorobenzoic acid, 2-amino-4,5-diethylbenzoic acid, 2-amino-4,5-dibromobenzoic acid, 2-amino-4,5-dibenzylbenzoic acid, there is obtained the corresponding 5-butoxy-1,4-dihydronaphthalene-1,4-endo-oxide, 5-methyl-1,4-dihydronaphthalene-1,4-endo-oxide, 5-chloro-1,4-dihydronaphthalene-1,4-endo-oxide, 5-bromo-1,4-dihydronaphthalene-1,4-endo-oxide, 5-benzyl-1,4-dihydronaphthalene-1,4-endo-oxide, 5-chlorobenzyl-1,4-dihydronaphthalene-1,4-endo-oxide, 5,8-diethyl-1,4-dihydronaphthalene-1,4-endo-oxide, 5,8-dichloro-1,4-dihydronaphthalene-1,4-endo-oxide, 5,8-dibenzyl-1,4-dihydronaphthalene-1,4-endo-oxide, 6-butyl-1,4-dihydronaphthalene-1,4-endo-oxide, 6-methyl-1,4-dihydronaphthalene-1,4-endo-oxide, 6-chloro-1,4-dihydronaphthalene-1,4-endo-oxide, 6,7-diethyl-1,4-dihydronaphthalene-1,4-endo-oxide, 6,7-dibromo-1,4-dihydronaphthalene-1,4-endo-oxide, 6,7-dibenzyl-1,4-dihydronaphthalene-1,4-endo-oxide.

EXAMPLE IV

1,4-Carbonyloxy-9,10-oxido-5- and 8-methoxy-1,4,9,9a,10,10a-hexahydroanthracene (VIIb)

5-Methoxy-1,4-dihydronaphthalene-1,4-endo-oxide (IIIb) (1.05 g) was dissolved in α-pyrone (VI) (0.578 g) with slight warming and the resulting mixture left to stand at room temperature under nitrogen for ten days. Ether was added and solid filtered off to give 1.35 g (83% yield of 1,4-carbonyloxy-9,10-oxido-5- and 8-methoxy-1,4,9,9a,10,10a-hexahydroanthracene (VIIb). The product can be purified by chromatography using florisil column eluted with 25% ether in hexane. m.p. 120° C. (decomp.)

nmr: (CDCl$_3$; 60 MHz) 7.38-6.50 (m, 5H), 5.35 (m, 2H), 5.13 (m, 1H), 3.83 (s, 3H), 3.83 (m, 1H), 2.75 (m, 1H), 2.32 (m, 1H).

ir: (KBr) 5.73

Analysis: Calculated for C$_{16}$H$_{14}$O$_4$: C, 71.11; H, 5.19. Found: C, 70.93; H, 5.84.

In accordance with the above procedure but where, in place of 5-methoxy-1,4-dihydronaphthalene-1,4-endo-oxide, there is employed 5-butoxy-1,4-dihydronaphthalene-1,4-endo-oxide, 5-methyl-1,4-dihydronaphthalene-1,4-endo-oxide, 5-chloro-1,4-dihydronaphthalene-1,4-endo-oxide, 5-bromo-1,4-dihydronaphthalene-1,4-endo-oxide, 5-benzyl-1,4-dihydronaphthalene-1,4-endo-oxide, 5-chlorobenzyl-1,4-dihydronaphthalene-1,4-endo-oxide, 5,8-diethyl-1,4-dihydronaphthalene-1,4-endo-oxide, 5,8-dichloro-1,4-dihydronaphthalene-1,4-endo-oxide, 5,8-dibenzyl-1,4-dihydronaphthalene-1,4-endo-oxide, 6-butyl-1,4-dihydronaphthalene-1,4-endo-oxide, 6-methyl-1,4-dihydronaphthalene-1,4-endo-oxide, 6-chloro-1,4-dihydronaphthalene-1,4-endo-oxide, 6,7-diethyl-1,4-dihydronaphthalene-1,4-endo-oxide, 6,7-dibromo-1,4-dihydronaphthalene-1,4-endo-oxide, 6,7-dibenzyl-1,4-dihydronaphthalene-1,4-endo-oxide, there is obtained the corresponding 1,4-carbonyloxy-9,10-oxido-5- and 8-butoxy-1,4,9,9a,10,10a-hexahydroanthracene, 1,4-carbonyloxy-9,10-oxido-5- and 8-methyl-1,4,9,9a,10,10a-hexahydroanthracene, 1,4-carbonyloxy-9,10-oxido-5- and 8-chloro-1,4,9,9a,10,10a-hexahydroanthracene, 1,4-carbonyloxy-9,10-oxido-5- and 8-bromo-1,4,9,9a,10,10a-hexahydroanthracene, 1,4-carbonyloxy-9,10-oxido-5- and 8-benzyl-1,4,9,9a,10,10a-hexahydroanthracene, 1,4-carbonyloxy-9,10-oxido-5- and 8-chlorobenzyl-1,4,9,9a,10,10a-hexahydroanthracene, 1,4-carbonyloxy-9,10-oxido-5,8-diethyl-1,4,9,9a,10,10a-hexahydroanthracene, 1,4-carbonyloxy-9,10-oxido-5,8-dichloro-1,4,9,9a,10,10a-hexahydroanthracene, 1,4-carbonyloxy-9,10-oxido-5,8-dibenzyl-1,4,9,9a,10,10a-hexahydroanthracene, 1,4-carbonyloxy-9,10-oxido-6- and 7-butyl-1,4,9,9a,10,10a-hexahydroanthracene, 1,4-carbonyloxy-9,10-oxido-6- and 7-methyl-1,4,9,9a,10,10a-hexahydroanthracene, 1,4-carbonyloxy-9,10-oxido-6- and 7-chloro-1,4,9,9a,10,10a-hexahydroanthracene, 1,4-carbonyloxy-9,10-oxido-6,7-diethyl-1,4,9,9a,10,10a-hexahydroanthracene, 1,4-carbonyloxy-9,10-oxido-6,7-dibromo-1,4,9,9a,10,10a-hexahydroanthracene, 1,4-carbonyloxy-9,10-oxido-6,7-dibenzyl-1,4,9,9a,10,10a-dihydroanthracene.

EXAMPLE V 5,8-Dihydro-1,4-dimethoxy-6-ethoxynaphthalene (XII)

To a suspension of 4a,5,8,8a-tetrahydro-6-ethoxy-1,4-naphthoquinone (XI) (6.6 g, 32 mmole) in 18 ml of absolute ethanol was added with stirring under N a solution of sodium ethoxide prepared from dissolving 22 g sodium in 45 ml absolute ethanol under nitrogen. The mixture was heated to reflux for ten minutes and cooled under N2 to room temperature. Methyl iodide (14.5 g) was added dropwise to the solution. After addition, the reaction mixture was heated to reflux for one hour and cooled to room temperature. Further cooling in ice bath resulted in a tan colored precipitate. The precipitate was separated by filtration and recrystalized from ethanol to give 5.87 g (78.5% yield) of 5,8-dihydro-1,4-dimethoxy-6-ethoxynaphthalene (XII), m.p. 102°–103° C.

nmr: (CDCl$_3$; 100 MHz) 6.63 (s, 2H), 4.76 (m, 1H), 3.80 (q, 2H), 3.76 (s, 6H), 3.31 (m, 4H), 1.28 (t, 3H)

ir: (KBr) no carbonyl absorption ms: m/e+ 234 (M+; 100%), 219 (6%), 205 (20%), 203 (55%), 189 (51%).

EXAMPLE VI 1,4-Dimethoxy-6-tetralone (XIII)

5,8-Dihydro-1,4-dimethoxy-6-ethoxynaphthalene (XII) (3.5 g, 15 mmole) was dissolved in 88 ml hot ethanol and then cooled to room temperature. The suspension was stirred with hydrochloric acid (2 N) (17.5 ml) for fifteen minutes. The reaction mixture was poured onto ice water and filtered to give as a tan solid 1,4-dimethoxy-6-tetralone (XIII) (2.67 g, 86.5% yield). m.p. 99°–100° C. (ethanol).

nmr: (CDCl$_3$) 6.68 (s, 2H), 3.78 (s, 3H), 3.76 (s, 3H), 3.48 (s, 2H), 3.04 (t, 2H), 2.50 (t, 2H).

ir: (KBr) 5.89 ms: m/e+ 206 (M+; 100%), 191 (11.1%), 178 (3.6%), 164 (65.1%).

EXAMPLE VII 1,4-Dimethoxy-6-ethynyl-6-hydroxy-5,8-dihydro-(7H)naphthalene (XIV)

Acetylene, purified by passing it first through a dry ice acetone trap, then through concentrated sulfuric acid, was bubbled rapidly through freshly distilled tetrahydrofuran (20 ml) under nitrogen for one hour. Ethylmagnesium bromide (50 ml, 3.15 M in ether, 15.8 mmole) was added slowly. The temperature was maintained between 28°–33° C. by cooling with a water bath. After the complete addition of ethylmagnesium bromide, the passage of the acetylene gas was continued and 1,4-dimethoxy-6-tetralone (XIII) (1.03 g, 5 mmole) in dry tetrahydrofuran (5,0 ml) was added with stirring. After addition, the passage of the acetylene was continued for an extra one hour and the reaction mixture was left stirring at room temperature overnight. The reaction mixture was quenched with saturated oxalic acid and extracted with chloroform. The chloroform extract was washed well with water, dried over anhydrous magnesium sulfate, and evaporated to dryness. The oil residue was triturated with ether to give 1,4-dimethoxy-6-ethynyl-6-hydroxy-5,8-dihydro-(7H)naphthalene (XIV) as a white solid, m.p. 103°–105° C. (ethanol).

nmr: (CDCl$_3$; 100 MHz) 6.62 (s, 2H), 3.78 (s, 6H), 2.95 (m, 4H), 2.40 (s, 1H), 2.16 (s, 1H), 2.02 (t, 2H)

ir: (KBr) 2.75; 3.02 ms: m/e+232 (M+; 100%), 214 (18.8%), 199 (7.4%), 175 (12.8%), 164 (43.7%).

EXAMPLE VIII 1,4-Dimethoxy-6-acetoxy-6-acetyl-5,8-dihydro-(7H)naphthalene (XV)

A mixture of 1,4-dimethoxy-6-ethynyl-6-hydroxy-5,8-dihydro-(7H)naphthalene (XIV) (2.0 g, 8.65 mmole) and mercuric acetate (15.85 g, 18.3 mmole) in ethyl acetate (850 ml) was stirred at room temperature under nitrogen overnight. Hydrogen sulfide was bubbled through until no more black precipitate was formed. The black precipitate was removed by filtering through a celite pad. The filtrate was washed with saturated sodium bicarbonate and water, and dried over anhydrous magnesium sulfate. Removal of solvent under reduced pressure gave 1,4-dimethoxy-6-acetoxy-6-acetyl-5,8-dihydro-(7H) naphthalene (XV) as an off-white solid (2.57 g). Recrystalization from ethanol gave 1,4-dimethoxy-6-acetoxy-6-acetyl-5,8-dihydro-(7H)naphthalene (2.4 g, 96% yield), m.p. 120°–122° C.

nmr: (CDCl$_3$; 100 MHz) 6.63 (s, 2H), 3.78 (s, 3H), 3.75 (s, 3H), 3.06-2.00 (m, 6H), 2.20 (s, 3H), 2.02 (s, 3H)

ir: (KBr) 5.79; 5.83 ms: m/e+ 292 (M+; 20.4%), 250 (1.9%), 232 (100%), 217 (25.8%), 207 (29.2%), 201 (38.1%), 189 (61.9%), 43 (84.7%).

Analysis: Calculated for C$_{16}$H$_{20}$O$_5$: C, 65.75; H, 6.85. Found: C, 65.90; H, 6.72.

In accordance with the above procedure but where, in place of mercuric acetate, there is utilized mercuric formate, propionate or butyrate, there is obtained the corresponding 6-formyloxy, 6-propionoxy or 6-butyroxy-6-acetyl-1,4-dimethoxy-5,8-dihydro-(7H)naphthalene.

EXAMPLE IX 5,8-Dihydro-6-acetyl-6-acetoxy-1,4-(7H)naphthaquinone (XVI)

To a solution of 1,4-dimethoxy-6-acetoxy-6-acetyl-5,8-dihydro-(7H)naphthalene (XV) (0.368 g) in dioxane (20 ml) was added argentic oxide (4 eq). The mixture was sonicated briefly to achieve an even dispersal of oxidant. The resulting solution was stirred vigorously with a magnetic stirrer and nitric acid (6N, 1.5 ml) was added in one portion. Stirring was continued until all the silver oxide was consumed (three to five minutes). The reaction mixture was diluted with water and extracted with chloroform. The chloroform extract was washed well with water, dried, and evaporated to dryness. The oil residue was tritrated with ethanol and petroleum ether to give a light yellow solid (0.312 g, 94.5% yield). Recrystalization from ethanol/petroleum ether gave 5,8-dihydro-6-acetyl-6-acetoxy-1,4-(7H)naphthaquinone (XVI) as bright yellow crystals, m.p. 86°–87° C.

nmr: (CDCl3; 100 MHz) 6.74 (s, 2H), 2.90 (m, 2H), 2.50 (m, 2H), 2.20 (m, 2H), 2.18 (s, 3H), 2.08 (s, 3H)

ir: (KBr) 5.82; 6.05; 6.24 ms: m/e+263 (M++1; 1%) 219 (23.2%), 202 (17.3%), 187 (3%), 178 (4.2%), 160 (8.5%), 43 (100%).

In accordance with the above procedure but where, in place of 1,4-dimethoxy-6-acetoxy-6-acetyl-5,8-dihydro-(7H) naphthalene, there is used any of the corresponding 1,4-dimethoxy-6-alkanoyloxy-6-acetyl-5,8-dihydronaphthalenes produced in Example VIII, there is obtained the corresponding 5,8-dihydro-6-acetyl-6-alkanoyl-1,4-(7H)naphthaquinone (XVI).

EXAMPLE X 5,5a,7,10,11a,12-Hexahydro-9-acetyl-9-acetoxy-5,12-oxido-6,11-(8H)naphthacenequinone (XXa) (anthracycline numbering)

5,8-Dihydro-6-acetyl-6-acetoxy-1,4-(7H) naphthoquinone (XVI) (0.262 g, 1 mmole) was dissolved in diglyme (10 ml) and heated at 140° C. under nitrogen for five minutes while the pentacyclic lactone (VIIa) (0.264 g, 1.1 mmole) was added in portions. After addition, the mixture was heated for two extra minutes, cooled to room temperature, and precipitated with water. The precipitate was filtered, washed well with water, and dried under reduced pressure to give 5,5a,7,10,-11a,12-hexahydro-9-acetonyl-9-acetyl-5,12-oxido-6,11-(8H)naphthacenequinone (XXa) (0.365 g, 96% yield).

nmr: (CDCl3; 100 MHz) 7.14 (m, 4H), 5.75 (m, 2H), 3.60 (m, 2H), 3.00–1.88 (m, 6H), 2.06 (s, 3H), 1.95 (s, 3H)

ir: (CHCl3) 5.77; 5.82; 6.00 ms: m/e+380 (M+; 0.2%) 337 (1.4%), 321 (0.3%), 295 (5.7%), 277 (1.4%), 118 (100%), 43 (60.7%).

In accordance with the above procedure but where, in place of 5,8-dihydro-6-acetyl-6-acetoxy-1,4-(7H)naphthoquinone, there is employed any one of the other 5,8-dihydro-6-acetyl-6-alkanoyloxy-1,4-(7H) naphthoquinones (XVI) produced in Example (IX), there is obtained the corresponding 5,5a,7,10,11a,12-hexahydro-9-acetyl-9-alkanoyloxy-5,12-oxido-6,11-(8H)naphthacenequinone (XXa).

EXAMPLE XI 5,5a,7,10,11a,12-Hexahydro-9-acetyl-9-acetoxy-4-methoxy (and 1-methoxy)-5,12-oxido-6,11-(8H)naphthacenequinone (XXb)

Diglyme was warmed in an oil bath under nitrogen at 145° C. 5,8-Dihydro-6-acetyl-6-aceoxy-1,4-(7H)naphthoquinone (XVI) was added and heated for five minutes (640 mgs) and pentacyclic lactone (VIIb) was added (660 mgs) in small portions while backflushing with nitrogen. After addition, the solution was stirred at 145° C. for five more minutes. The mixture was cooled to room temperature and poured into water. The cloudy water layer was extracted with ethyl acetate. The organic layer was washed three times with water and then with saturated saline. Concentration, followed by addition of water, gave an off-white oily solid which was washed several times with water and pumped dry.

nmr: Showed a very complex mixture of regioisomers ir: (CHCl3) 5.79; 6.02

The mixture was directly aromatized as in Example XIII.

The foregoing procedure may be carried out with any of the other pentacyclic lactones produced in accordance with Example IV to provide the corresponding 1-butoxy-(and 4-butoxy)-; 1methyl-(and 4-methyl)-; 1-chloro-(and 4-chloro)-; 1-bromo-(and 4-bromo)-; 1-benzyl-(and 4-benzyl)-; 1-chlorobenzyl-(and 4-chlorobenzyl)-; 1,4-diethyl; 1,4-dichloro; 1,4-dibenzyl; 2-butyl-(and 3-butyl)-; 2-methyl(and 3-methyl)-; 2-chloro-(and 3-chloro)-; 2,3-dimethyl-; 2,3-dibromo-; and 2,3-dibenzyl-9-acetyl-9-acetoxy-5,12-oxido-5, 5a,7,10,-11a,12-hexahydro-6,11-(8H)naphthacenequinones (XX) which are similarly aromatized as in Example XIII.

EXAMPLE XII 7,10-Dihydro-9-acetoxy-9-acetyl-6,11-(8H) naphthacenequinone (XXIa)

A mixture of 5,5a,7,10,11a,12-hexahydro-9-acetyl-9-acetoxy-5,12-oxido-6,11-(8H)naphthacenequinone (XXa) (0.360 g, 0.95 mmole) and anhydrous sodium acetate (0.155 g, 1.9 mmole) in acetic acid (10 ml) was heated at reflux under nitrogen for sixteen hours, and cooled to room temperature. The mixture was precipitated with water. The precipitate was washed well with water, dried under reduced pressure to give a yellowish solid. Chromatography on silica gel gave the yellow solid identified as 7,10-dihydro-9-acetyl-6,11-(8H)naphthacenequinone (XXIa), (0.2312g, 67% yield), m.p. 254°–256° C. (from acetic acid)

nmr: (CDCl3; 100 MHz) 8.70 (s, 2H), 8.12 (m, 2H), 7.74 (m, 2H), 3.14 (m, 2H), 3.0–2.0 (m, 4H), 2.25 (s, 3H), 2.11 (s, 3H)

ir: (CDCl3) 5.77; 5.82; 6.01 ms: m/e+362 (M+; 1.9%), 320 (5%), 302 (49.6%), 277 (100%), 259 (19.2%), 249 (17.3%), 118 (77.7%), 43 (62.5%).

EXAMPLE XIII 7,10-Dihydro-9-acetoxy-9-acetyl-4-methoxy(and 1-methoxy)-6,11-(8H)naphthacenequinone (XXIb) (regioisomeric mixture)

The product of Example XI was dissolved in acetic acid (25 ml) with sodium acetate (anh.) (410 mgs). The reaction mixture was placed under nitrogen and refluxed for five hours. The mixture was then cooled and poured into water. The aqueous phase was extracted three times with chloroform. The organic layer was washed several times with water and once with saturated saline. Concentration and chromatography on silica gel (5:1 chloroform/ethyl acetate) gave 540 mgs of orange solid as 7,10-dihydro-9-acetoxy-9-acetyl-4-methoxy (and 1-methoxy)-6,11-(8H)naphthacenequinone (XXIb) (regioisomeric mixture), (57% from VIIb, m.p. 221°–223° C.) (sealed tube, decomp.).

nmr: (CDCl3; 100 MHz) 9.11 (s, 1H), 8.58 (s, 1H), 7.64 (m, 2H), 7.04 (m, 1H), 4.03 (s, 3H), 3.3 to 2.1 (m, 6H), 2.16 (s, 3H), 2.08 (s, 3H)

ir: (CHCl3) 5.78; 5.99; 6.15 uv (abs. EtOH) 246; 440 nm ms: m/e+ 392 (M+), 346, 332, 330, 307

In accordance with the above procedure, but starting with any of the products of Example XI, there is obtained the corresponding 1-butoxy-(and 4-butoxy)-; 1-methyl-(and 4-methyl)-; 1-chloro-(and 4-chloro)-; 1-bromo-(and 4-bromo)-; 1-benzyl-(and 4-benzyl)-; 1- chlorobenzyl-(and 4-chlorobenzyl)-; 1,4-diethyl-; 1,4-dichloro-; 1,4-dibenzyl-; 2-butyl-(and 3-butyl)-; 2-methyl-(and 3-methyl)-; 2-chloro-; (and 3-chloro)-; 2,3-dimethyl-; 2,3-dibromo-; and 2,3-dibenzyl-9-acetyl-9-acetoxy-7,10-dihydro-6,11-(8H) naphthacenequinones (XXI).

EXAMPLE XIV 7,10-Dihydro-9-acetyl-6,9,11-trihydroxy-(8H)naphthacene-6,9,11-triacetate (XXIIa)

A suspension of 7,10-dihydro-9-acetoxy-9-acetyl-6,11-(8H) naphthacenequinone (XXIa) (9.5 mg) and excess zinc dust in acetic anhydride (1 ml) was heated at 110° C. under nitrogen for twenty minutes. Yellow color disappeared during the reaction. The zinc dust was removed by filtering the reaction mixture through a celite pad. The excess acetic anhydride was hydrolyzed with warm water. The resulting solution was extracted with chloroform and the chloroform extract washed well with water, then dried over anhydrous sodium sulfate. The solvent was removed under reduced pressure to give an oily residue. The residue was chromatographed with silica prep plates eluting with 1% methanol/chloroform to give a light colored oil which solidified by triturating with chloroform and hexane. The solid was collected and identified as 7,10-dihydro-9-acetyl-6,9,11-trihydroxy-(8H)naphthacene-6,9,11-triacetate (XXIIa) (10.9 mg, 92.4% yield).

nmr: (CDCl$_3$; 100MHz), 8.28 (s, 2H), 7.95 (m, 2H), 7.47 (m, 2H), 3.29 (m, 2H), 2.88 (m, 2H), 2.75–2.00 (m, 2H), 2.57 (s, 6H), 2.23 (s, 3H), 2.00 (s, 3H)

ir: (CDCl$_3$) 5.66; 5.72; 5.80 ms: m/e+ 448 (M+; 12.1%), 406 (22.6%), 388 (3.0%), 364 (14.0%), 346 (28.1%), 320 (2.33%), 304 (100%), 278 (14.4%), 263 (21.5%), 262 (21.2%), 32 (29.8%)

In accordance with the above procedure but where, in place of acetic anhydride, there is utilized an alkanoic anhydride of the group propionic anhydride, butyric anhydride or valaric anhydride, there is obtained the corresponding 7,10-dihydro-9-acetyl-1,6,9,11-trihydroxy-(8H)naphthacene-6,11-dialkanoate-9-acetate (XXII).

EXAMPLE XV 7,10-Dihydro-9-acetyl-6,9,11-trihydroxy-4-methoxy-(and 1-methoxy)-(8H)naphthacene-6,9,11-triacetate (XXIIb) (regioisomeric mixture)

The product of Example XIII, the quinone (XXIb) (230 mg) was heated with zinc dust in acetic anhydride under nitrogen at 110° C. for about twenty minutes. Color changed from red to yellow. The reaction mixture was filtered through celite, and the filtrate diluted with hot water, and then cooled and extracted three times with chloroform. The organic layer was then washed thoroughly with water and once with saturated saline. The filtrate was dried briefly over anhydrous sodium sulfate, concentrated, and chromatographed on silica gel. Elution with chloroform/methanol gave 180 mgs (70% yield) of unstable 7,10-dihydro-9-acetyl-6,9,11-trihydroxy-4-methoxy(and 1-methoxy)-(8H)naphthacene-6,9,11-triacetate (XXIIb), regioisomeric mixture, as a yellow oil which was stored at 0° C.

nmr: (CDCl$_3$; 100 MHz) 8.80 (s, 1H), 8.30 (s, 1H), 7.51 (m, 2H), 6.78 (t, 1H), 4.08 (s, 3H), 3.3 to 2.1 (m, 6H), 2.59 (s, 6H), 2.25 (s, 3H), 2.02 (s, 3H)

ir: (CHCl$_3$) 5.70; 5.78 ms: m/e+ 478 (M+), 436, 418, 394, 376, 334 uv (abs. EtOH) 222, 264, 378, 400 nm

The foregoing procedure may be carried out with any of the other naphthacenequinones produced in accordance with Example XIII to provide the corresponding 1-butoxy-(and 4-butoxy)-; 1-methyl-(and 4-methyl)-; 1-chloro-(and 4-chloro)-; 1-bromo-(and 4-bromo)-; 1-benzyl-(and 4-benzyl)-; 1-chlorobenzyl-(and 4-chlorobenzyl)-; 1,4-diethyl-; 1,4-dichloro-; 1,4-dibenzyl-; 2-butyl-(and 3-butyl)-; 2-methyl-(and 3-methyl)-; 2-chloro-(and 3-chloro)-; 2,3-dimethyl-; 2,3-dibromo-; and 2,3-dibenzyl-9-acetyl-6,9,11-trihydroxy-7,10-dihydro-(8H)naphthacene-6,9,11-triacetates (XXII).

EXAMPLE XVI (+)-4-Demethoxy-7-deoxydaunomycinone-6,9,11-triacetate (XXIIIa)

A mixture of chromium trioxide (7 mg) in 80% acetic acid (0.5 ml) was added to a solution of 7,10-dihydro-6,9,11-trihydroxy-9-acetyl-(8H)naphthacene-6,9,11-triacetate (XXIIa) (7.2 mg) in acetic acid (1 ml) at room temperature under nitrogen. After addition, the solution was stirred for two hours and diluted with water. The resulting mixture was then extracted with chloroform. The chloroform extract was washed well with water and dried over anhydrous sodium sulfate. The solvent was removed under reduced pressure to give an oily residue. The residue was chromatographed on silica gel (chloroform/1% methanol) to give a light colored oil which solidified on triturating with chloroform and hexane. The solid was collected and identified as (+)-4-demethoxy-7-deoxydaunomycinone-6,9,11-triacetate (XXIIIa) (5.3 mg, 64% yield). mp 247°–248° C. (EtOAc - CCl$_4$)

nmr: (CDCl$_3$; 100 MHz) 8.16 (m, 2H), 7.74 (m, 2H), 3.24 (m, 2H), 2.91 (m, 2H), 2.64–2.32 (m, 2H), 2.53 (s, 6H), 2.23 (s, 3H), 2.04 (s, 3H)

ir: (CHCl$_3$) 5.65; 5.75; 5.80; 5.97 ms: m/e+ 478 (M+; 0.1%), 436 (1.4%), 418 (0.4%), 394 (11%), 376 (9.4%), 351 (2%), 334 (100%), 316 (11.2%), 309 (19%), 301 (6.8%), 291 (22.5%), 43 (60%)

EXAMPLE XVII (+)-7-Deoxydaunomycinone-6,9,11-triacetate(and the 1-methoxy regioisomer thereof) (XXIIb)

7,10-Dihydro-9-acetyl-4-methoxy(and 1-methoxy)-6,9,11-trihydroxy-(8H)naphthacene-6,9,11-triacetate (XXIIb) (110 mgs) was dissolved in acetic acid (15 ml), cooled in a water bath, and placed under nitrogen. Chromium trioxide (110 mgs) in 80% acetic acid (15 ml) was added slowly dropwise. The mixture was stirred at room temperature. After two hours, it was poured into water and the water was extracted three times with chloroform and once with ethyl acetate. The combined organic phase was washed with water five times, once with saturated saline, and dried briefly over sodium sulfate. Concentration and chromatography on silica gel (5:1 chloroform/methanol) gave 7-deoxydaunomycinone-6,9,11-triacetate (and the 1-methoxy regioisomer thereof) (XXIIIb) (11 mg, 10%) as a yellow oil.

nmr: CDCl$_3$; 100 MHz) 7.7 to 6.9 (m, 3H), 3.90 (s, 3H), 3.2 to 2.2 (m, 6H), 2.41 (s, 6H), 2.17 (s, 3H), 1.98 (s, 3H)

ir: (CHCl$_3$) 5.70, 5.78, 6.01 ms: m/e+ 424 (loss of 2 ketene) 364 (loss of 2 ketene + HOAc) (348) (346) (321) (231)

uv (Abs EtOH) 258, 380

The foregoing procedure may be carried out with any of the other dihydronaphthacenetriacetates produced in accordance with Example XV to provide the corresponding 1-butoxy-(and 4-butoxy)-; 1-methyl-(and 4-methyl)-; 1-chloro-(and 4-chloro)-; 1-bromo-(and 4-bromo)-; 1-benzyl-and 4-benzyl)-; 1-chlorobenzyl-(and 4-chlorobenzyl)-; 1,4-diethyl-; 1,4-dichloro-; 1,4-dibenzyl-; 2-butyl-(and 3-butyl)-; 2-methyl-(and 3-methyl)-; 2-chloro-(and 3-chloro)-; 2,3-dimethyl-; 2,3-dibromo-; and 2,3-dibenzyl-7-deoxy-4-demethoxydaunomycinone-6,9,11-triacetate (XXIII).

EXAMPLE XVIII (±)-4-Demethoxy-7-deoxydaunomycine (XXIVa)

(±)-4-Demethoxy-7-deoxydaunomycinone-6,9,11-triacetate (XXIIIa) (12 mg) was dissolved in acetic acid (5 ml) and mixed with 6N hydrochloric acid (5 ml) at 65°–75° C. under nitrogen. The resulting mixture was heated at 75° C. for two hours, cooled to room temperature, and diluted with water. The solution was extracted with chloroform. The chloroform extract was washed well with water and dried over anhydrous sodium sulfate. The solvent was removed under reduced pressure to give (±)-4-demethoxy-7-deoxydaunomycinone (XXIVa) as a red solid (8.78 mg, 100% yield).

nmr: (CDCl$_3$) 13.54 (s, 2H), 8.36 (m, 2H), 7.84 (m, 2H), 3.71 (s, broad, 1H), 2.99 (m, 4H), 2.40 (s, 3H), 1.96 (m, 2H)

ir: (KBr) 5.88; 6.17; 6.31 ms: m/e$^+$ 352 (M$^+$, 17.3%), 334 (18.3%), 309 (100%), 291 (24.7%)

The (±)-4-Demethoxy-7-deoxydaunomycinone (XXIVa) from the above reaction was identical in all respects with The same substance independently prepared as in U.S. Pat. No. 4,021,457.

EXAMPLE XIX (±)7-Deoxydaunomycinone (and its 1-methoxy regioisomer) (XXIVb)

7-deoxydaunomycinone-6,9,11-triacetate (and its 1-methoxy regioisomer) (XXIIIb) (7 mgs) was heated in acetic acid (1 ml) and 6N hydrochloric acid (1 ml) at 75° C., under nitrogen, for two hours. The resulting red solution was poured into water and extracted with chloroform. The chloroform layer was washed repeatedly with water and then once with saturated saline, and then dried briefly over sodium sulfate. Concentration and chromatography on silica gel (5:1 chloroform ethyl acetate) gave racemic 7-deoxydaunomycinone (5.8 mgs, 94% yield) as an orange solid identical in all respects to a sample of racemic 7-deoxydaunomycinone previously prepared by an independent route. (J. Am. Chem. Soc., 98 1967 (1976)).

The foregoing procedure may be carried out with any of the other 4-demethoxy-7-deoxydaunomycinone triacetates (XXIII) produced in accordance with Example XVII to provide the corresponding 1-butoxy-(and 4-butoxy)-; 1-methyl-(and 4-methyl)-; 1-chloro-(and 4-chloro)-; 1-bromo-(and 4-bromo)-; 1-benzyl-(and 4-benzyl)-; 1-chlorobenzyl-(and 4-chlorobenzyl)-; 1,4-diethyl-; 1,4-dichloro-; 1,4-dibenzyl-; 2-butyl-(and 3-butyl)-; 2-methyl-(and 3-methyl)-; 2-chloro- and 3-chloro)-; 2,3-dimethyl-; 2,3-dibromo-; and 2,3-dibenzyl-4-demethoxy-7-deoxydaunomycinones (XXIV).

EXAMPLE XX

13-Ethylenedioxy ketal of 9,10-dihydro-9-acetyl-6,9,11-trihydroxy-(8H)naphthacene-6,9,11-triacetate (XXVIa)

9,10-Dihydro-9-acetyl-6,9,11-trihydroxy-(8H) naphthacene-6,9,11-triacetate (0.024 mmole) is taken up in benzene (10 ml), ethylene glycol (1 ml) and anhydrous p-toluene sulfonic acid (1 mg) is added thereto and the mixture stirred vigorously under reflux for 36 hours. Water which forms in the ketalization is removed during this period by the aid of a Dean and Stark moisture test receiver. Saturated aqueous sodium bicarbonate (2.5 ml) is added to the cooled reaction mixture which is then transferred to separatory funnel where it is diluted with water (10 ml). The organic layer is separated, the aqueous layer further extracted (three times, 10 ml) with more benzene, the combined benzene extract washed with water, dried over potassium carbonate and filtered. The solvent is removed under reduced pressure to yield the 13-ethylenedioxy ketal of 9,10-dihydro-9-acetyl-6,9,11-trihydroxy-(8H)naphthacene-6,9,11-triacetate (XXVIa).

The residue is then taken up in a mixture of acetic anhydride (5 ml) and pyridine (5 ml) and the resultant solution allowed to stand at ambient temperature overnight. The mixture is poured onto ice water and extracted with benzene. The benzene layer is washed with 2N aqueous hydrochloric acid and saturated sodium bicarbonate and then the solvent removed under reduced pressure. This procedure will re-acylate any of the hydroxy groups which have become de-acylated during the ketalization step.

EXAMPLE XXI (±)-Demethoxy-7-oxo-7-deoxydaunomycinone-6,9,11-triacetate-13-ethylene ketal (XXVIIa)

A mixture of chromium trioxide (21 mg) in glacial acetic acid (1.0 ml) is added to a solution of 7,10-dihydro-6,9,11-trihydroxy-9-acetyl-(8H)naphthacene-6,9,11-triacetate-13-ethylene ketal (XXVIa) (14 mg) in glacial acetic acid (1 ml) at room temperature under nitrogen. The mixture is stirred at room temperature for 16 hours, diluted with water, and extracted with chloroform. The chloroform extract is thoroughly washed with water and dried over anhydrous sodium sulfate. The solvent is removed under reduced pressure to give an oily residue. The residue is chromatographed on silica gel preparative TLC plates, elution with methanol in methylene chloride (1:99) yields (±)4-demethoxy-7-oxo-7-deoxydaunomycinone-6,9,11-triacetate-13-ethylene ketal (XXVIIa).

EXAMPLE XXII (±)-4-Demethoxydaunomycinone (XXVa)

To isopropanol (5 ml) is added sodium hydroxide (10 mg) and sodium borohydride (20 mg) with cooling. To this solution is added a solution of (±)4-demethoxy-7-oxo-7-deoxydaunomycinone-6,9,11-triacetate-13-ethylene ketal (XXVIIa) (0.5 mmole) in isopropanol (2 ml). The reaction mixture is heated to reflux and allowed to stand, in an inert atmosphere, overnight. The reaction mixture is then diluted with aqueous sodium hydroxide (1 N, 10 ml) and extracted with chloroform. The extract is washed with water, dried over anhydrous sodium sulfate, and evaporated to yield a residue which is taken up in trifluoroacetic acid (5 ml) and the solution allowed to stand for two hours at room temperature. The reaction mixture is poured into water, extracted with chloroform, the chloroform washed well with water, and then dried over sodium sulfate.

The residue is dissolved in aqueous hydrochloric acid (1 N, 5 ml) and the solution heated for two hours on a steam bath. After basification with concentrated aqueous ammonium hydroxide, the solution is extracted with methylene chloride (four times, 5 ml), the combined extract washed with water (two times, 5 ml), dried over sodium sulfate and evaporated under reduced pressure to yield a residue, which on chromatography on silica prep plate (elution with 3% methanol/methylene chloride) gives (±)-4-demethoxydaunomycinone (XXVa) as the major product.

EXAMPLE XXIII

The procedures of Examples XX through XXII may be carried out with any of the naphthacenequinones produced in accordance with Example XV to provide (±)-daunomycinone, (±)-1-methoxy-4-demethoxydaunomycinone, and the corresponding (±)-4-butoxy-(and 1-butoxy)-; 4-methyl-(and 1-methyl)-; 4-chloro-(and 1-chloro)-; 4-bromo-(and 1-bromo)-; 4-benzyl-(and 1-benzyl)-; 4-chlorobenzyl-(and 1-chlorobenzyl)-; 1,4-diethyl-; 1,4-dichloro-; 1.4-dibenzyl-; 2-butyl-(and 3-butyl)-; 2-methyl-(and 3-methyl)-; 2-chloro-(and 3-chloro)-; 2,3-dimethyl-; 2,3-dibromo-; and 2,3-dibenzyl-9-acetyl-6,9,11-trihydroxy-7,10-dihydro-5,12-(8H)naphthacenedione (XXVb).

EXAMPLE XXIV

Direct resin oxidation of 9-ethynyl-7,10-dihydro-6,9,11-trihydroxy-5,12-(8H)naphthacenedione 9-Ethynyl-7,10-dihydro-6,9,11-trihydroxy-5,12-(8H)naphthacenedione (500 mg) was suspended in methanol (125 ml) and water (25 ml). Mercury (II)-Resin (5 g, prepared by the method of M. S. Newman, JACS, 75, 4740 (1953), substituting Amberlite CG-120 for Dowex-50) was added, and the reaction was heated at reflux with stirring and monitored by tlc until no starting material remained (approximately 20 hours). The reaction mixture was filtered, and the filter cake was washed with chloroform until all colored material was removed. The filtrate was poured into water, the two phases were separated, and the aqueous phase was extracted with several portions of chloroform. The combined extracts were washed with water and saturated saline, dried over sodium sulfate, and the solvent was removed under reduced pressure. Chromatography over silica gel (~250 g) eluting with methylene chloride and gradually changing to methanol/methylene chloride (3:97) yielded (±)-4-demethoxy-7-deoxydaunomycinone (460 mg).

In accordance with the above procedure but where, in place of 9-ethynyl-7,10-dihydro-6,9,11-trihydroxy-5,12-(8H)naphthacenedione, there is utilized the corresponding 4-methoxy-(or 1-methoxy)-; 4-butoxy-(and 1-butoxy)-; 4-methyl-(and 1-methyl)-; 4-chloro-(and 1-chloro)-; 4-bromo-(and 1-bromo)-; 4-benzyl-(and 1-benzyl)-; 4-chlorobenzyl-(and 1-chlorobenzyl)-; 1,4-diethyl-; 1,4-dichloro-; 1,4-dibenzyl-; 2-butyl-(and 3-butyl)-; 2-methyl-(and 3-methyl)-; 2-chloro-(and 3-chloro)-; 2,3-dimethyl-; 2,3-dibromo-; and 2,3-dibenzyl-9-ethynyl-6,9,11-trihydroxy-7,10-dihydro-5,12-(8H)-naphthacenedione to yield (±)-7-deoxydaunomycinone (and its 1-methoxy regioisomer) and the corresponding (±)-4-butoxy-(and 1-butoxy)-; 4-methyl-(and 1-methyl)-; 4-chloro-(and 1-chloro)-; 4-bromo-(and 1-bromo)-; 4-benzyl-(and 1-benzyl)-; 4-chlorobenzyl-(and 1-chlorobenzyl)-; 1,4-diethyl-; 1,4-dichloro-; 1,4-dibenzyl-; 2-butyl-(and 3-butyl)-; 2-methyl-(and 3-methyl)-; 2-chloro-(and 3-chloro)-; 2,3-dimethyl-; 2,3-dibromo-; and 2,3-dibenzyl-4-demethoxy-7-deoxydaunomycinone.

EXAMPLE XXV

Resolution of (±)-demethoxy-7-deoxydaunomycinone (XXIVa)

(±)-4-Demethoxy-7-deoxydaunomycinone (10 mg) and (R)-2-aminoxy-4-methylvaleric acid (5 mg) were suspended in a methanol-pyridine (10:1) mixture (2.5 ml). The mixture was stirred at room temperature for 24 hours, then poured into 0.1 N hydrochloric acid and extracted with chloroform. The extracts were combined, washed with water, dried over anhydrous sodium sulfate, and the solvent was removed under reduced pressure. The residue was spotted on a thin tlc plate and eluted three times with 1% glacial acetic acid in 3% methanol/methylene chloride (3:97) to give two product bands.

Each of the two oximes obtained by the above procedure was hydrolyzed by the following procedure:

The oxime was dissolved in trifluoroacetic acid (2 ml) and treated with 37% formaldehyde (1 ml). The reaction was stirred at room temperature for five hours, then poured into water and extracted with chloroform. The combined extracts were washed with saturated sodium bicarbonate, water, and dried over anhydrous sodium sulfate. Mass spectra and tlc show the material to be 4-demethoxy-7-deoxydaunomycinone.

CD spectra of the two compounds show that the less polar oxime has 9(S) stereochemistry.

The foregoing procedure may be carried out with any of the naphthacenequinones produced in accordance with Example XIX or XXIV to provide, in resolved form, the stereoisomers of 7-deoxydaunomycinone (and its 1-methoxy regioisomer) and the corresponding 4-butoxy-(and 1-butoxy)-; 4-methyl-(and 1-methyl)-; 4-chloro-(and 1-chloro)-; 4-bromo-(and 1-bromo)-; 4-benzyl-(and 1-benzyl)-; 4-chlorobenzyl-(and 1-chlorobenzyl)-; 1,4-diethyl-; 1,4-dichloro-; 1,4-dibenzyl-; 2-butyl-(and 3-butyl)-; 2-methyl-(and 3-methyl)-; 2-chloro-(and 3-chloro)-; 2,3-dimethyl-; 2,3-dibromo-; and 2,3-dibenzyl-9-acetyl-6,9,11-trihydroxy-7,10-dihydro-5,12-(8H)naphthacenedione (XXIV).

We claim:
1. A compound of the formula

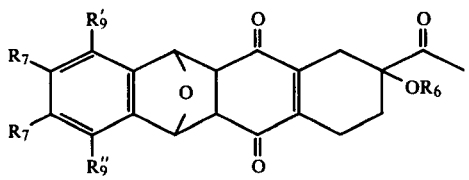

wherein
$R_6$ is lower alkanoyl or phenyl lower alkanoyl,
$R_7$ is hydrogen, lower alkyl, or halogen of the group chlorine and bromine,
$R_9'$ and $R_9''$ is hydrogen, lower alkyl, or lower alkoxy, phenyl- or substituted phenyl lower alkyl wherein the substituent groups are lower alkyl, lower alkoxy or halo,
wherein the term lower alkyl or lower alkoxy signifies a group containing a straight or branch chain hydrocarbon moiety containing 1 to 5 carbon atoms in the chain, or halogen of the group chlorine and bromine, provided that where one of $R_9'$ or $R_9''$ is lower alkoxy, the other has one of the alternate values given hereinabove, further provided that where both $R_7$ groups are other than hydrogen, one of $R_9'$ and $R_9''$ is hydrogen and where $R_9'$ or $R_9''$ is other than hydrogen, $R_7$ is hydrogen.

2. A tetrahydronaphthaquinone of the formula

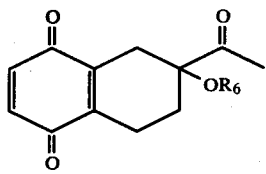

wherein $R_6$ is as in claim 1.

3.

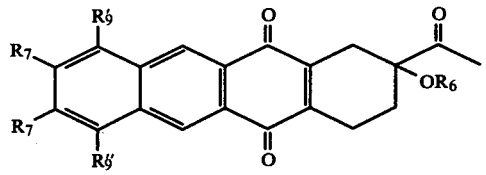

wherein $R_6$, $R_7$ and $R_9'$ and $R_9''$ are as in claim 1.

4.

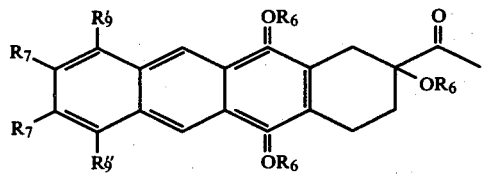

wherein $R_6$, $R_7$ and $R_9'$ and $R_9''$ are as in claim 1.

5.

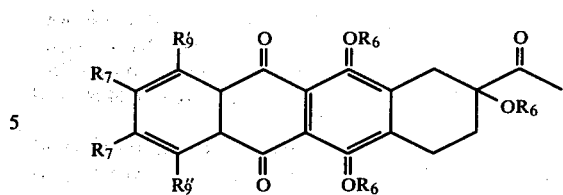

wherein $R_6$, $R_7$ and $R_9'$ and $R_9''$ are as in claim 1.

6. The process of preparing a compound of the formula

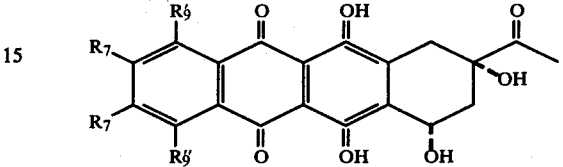

$R_7$ is hydrogen, lower alkyl, or halogen of the group chlorine and bromine, $R_9'$ and $R_9''$ is hydrogen, lower alkyl, or lower alkoxy, phenyl or substituted phenyl lower alkyl wherein the substituent groups are lower alkyl, lower alkoxy or halo, wherein the term lower alkyl or lower alkoxy signifies a group containing a straight or branch chain hydrocarbon moiety containing 1 to 5 carbon atoms in the chain or halogen of the group chlorine and bromine, provided that where one of $R_9'$ or $R_9''$ is lower alkoxy, the other has one of the alternate values given hereinabove, further provided that where both $R_7$ groups are other than hydrogen, one of $R_9'$ and $R_9''$ is hydrogen, and where $R_9'$ or $R_9''$ is other than hydrogen, $R_7$ is hydrogen,
which comprises the sequential steps of
 a. reacting a compound of claim 4 with an alkylene glycol in the presence of a catalytic amount of acid to form a ketal;
 b. oxidizing said ketal with more than four equivalents of chromium trioxide to form the corresponding naphthacene 5,7,12, trione ketal;
 c. reducing said 5,7,12 trione ketal with sodium borohydride to yield the 5,12-trione-7-hydroxy ketal;
 d. treating said product of step (c) with trifluoroacetic acid and aqueous mineral acid to yield the desired product.

* * * * *